United States Patent [19]

Kuslich

[11] Patent Number: 5,059,193
[45] Date of Patent: Oct. 22, 1991

[54] EXPANDABLE SPINAL IMPLANT AND SURGICAL METHOD

[75] Inventor: Stephen D. Kuslich, Maplewood, Minn.

[73] Assignee: Spine-Tech, Inc., Minneapolis, Minn.

[21] Appl. No.: 510,952

[22] Filed: Apr. 19, 1990

Related U.S. Application Data

[63] Continuation-in-part of Ser. No. 439,560, Nov. 20, 1989, abandoned.

[51] Int. Cl.$^5$ .............................................. A61F 5/04
[52] U.S. Cl. ...................................... 606/61; 128/69; 606/60; 606/62; 606/63; 606/77
[58] Field of Search ...................... 128/69; 606/60–64, 606/68, 72, 73, 77; 623/16, 17, 18; 433/173, 177

[56] References Cited

U.S. PATENT DOCUMENTS

| | | | |
|---|---|---|---|
| 4,011,602 | 3/1977 | Rybicki et al. | 606/72 X |
| 4,275,490 | 6/1981 | Bivins | 606/72 X |
| 4,309,777 | 1/1982 | Patil | 606/61 X |
| 4,349,921 | 9/1982 | Kuntz | 623/17 |
| 4,379,451 | 4/1983 | Getscher | 606/68 |
| 4,501,269 | 2/1985 | Bagby | 623/18 X |
| 4,599,086 | 7/1986 | Doty . | |
| 4,611,581 | 9/1986 | Steffee | 606/73 X |
| 4,636,217 | 1/1987 | Ogilvie et al. . | |
| 4,657,550 | 4/1987 | Daher . | |
| 4,716,893 | 1/1988 | Fischer et al. | 606/73 X |
| 4,759,769 | 7/1988 | Hedman et al. | 623/17 |
| 4,772,287 | 9/1988 | Ray . | |
| 4,796,612 | 1/1989 | Reese | 606/72 |
| 4,834,752 | 5/1989 | Van Kampen . | |
| 4,834,757 | 5/1989 | Brantigan . | |
| 4,865,604 | 9/1989 | Rogozinski | 623/23 X |
| 4,874,389 | 10/1989 | Downey | 623/17 |
| 4,932,975 | 6/1990 | Main et al. | 606/61 X |
| 4,936,848 | 6/1990 | Bagby | 623/18 X |
| 5,015,255 | 5/1991 | Kuslich . | |

FOREIGN PATENT DOCUMENTS

| | | | |
|---|---|---|---|
| 3509417 | 9/1986 | Fed. Rep. of Germany | 606/73 |
| 0728855 | 5/1980 | U.S.S.R. | 433/176 |
| 8909030 | 10/1989 | World Int. Prop. O. | 606/73 |

OTHER PUBLICATIONS

Page from unidentified German Article with an attached English translation identifying pieces which are placed between vertebra.

*Primary Examiner*—Richard J. Apley
*Assistant Examiner*—Linda C. Dvorak
*Attorney, Agent, or Firm*—Merchant, Gould, Smith, Edell, Welter & Schmidt

[57] ABSTRACT

An expandable spinal implant is disclosed. The implant includes a plurality of ribs which are deformable between first and second states. In the first state, the ribs present a generally cylindrical implant. In the expanded second state, the ribs are arced outwardly to define a generally spherical implant. A tie mechanism is provided for urging the ribs between the first and second states and for holding the ribs in the expanded state. A novel surgical method is disclosed for stabilizing the spine by inserting the implant in the first state between opposing vertebrae and expanding the implant to the second state.

29 Claims, 7 Drawing Sheets

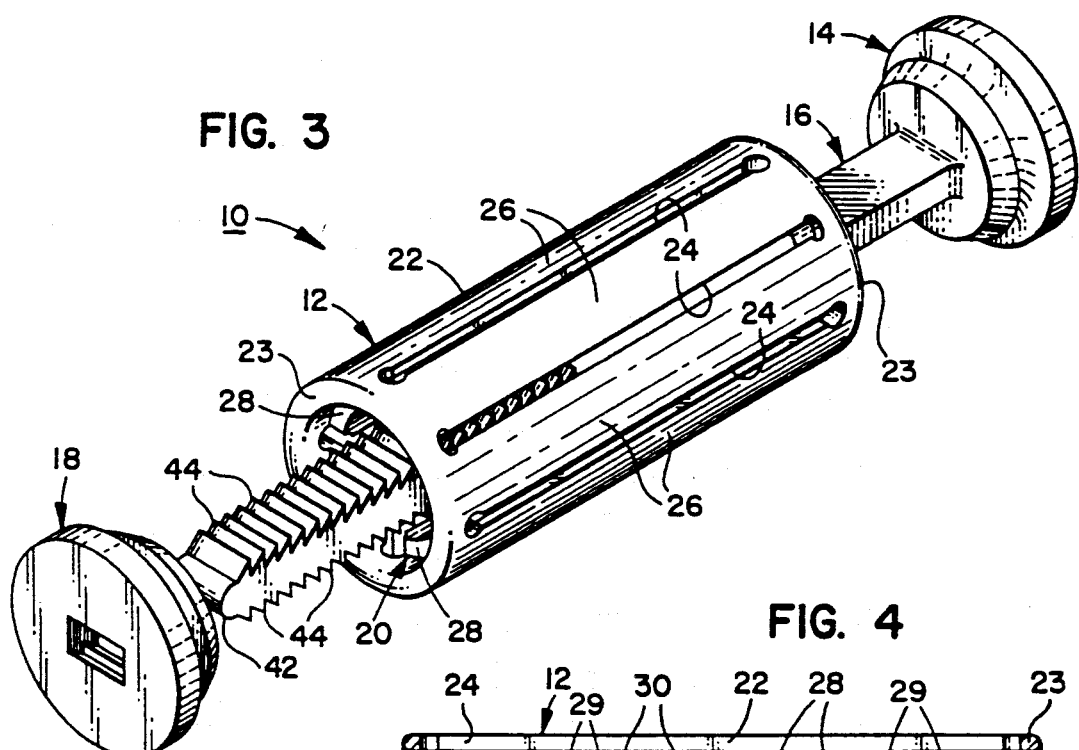
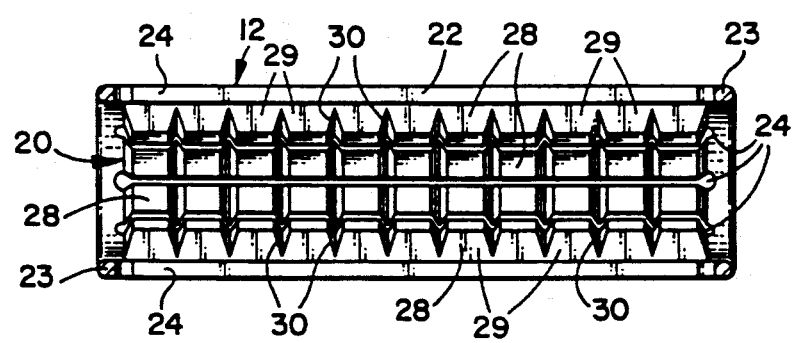
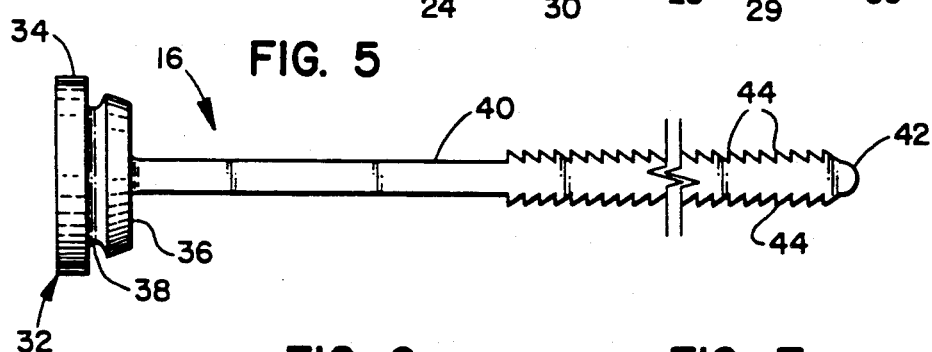
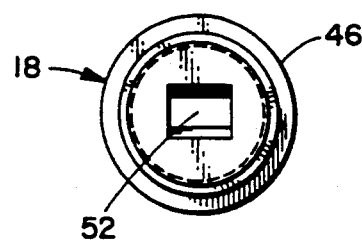
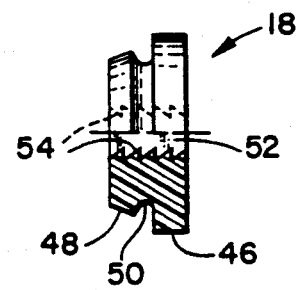

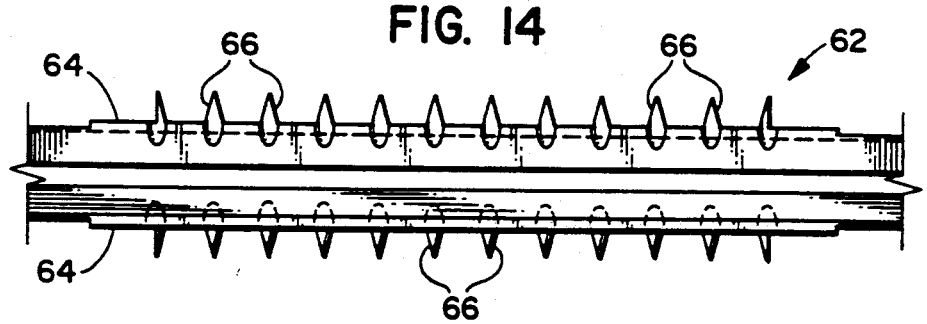
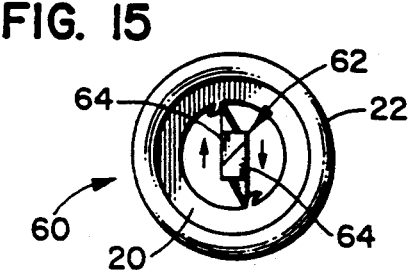
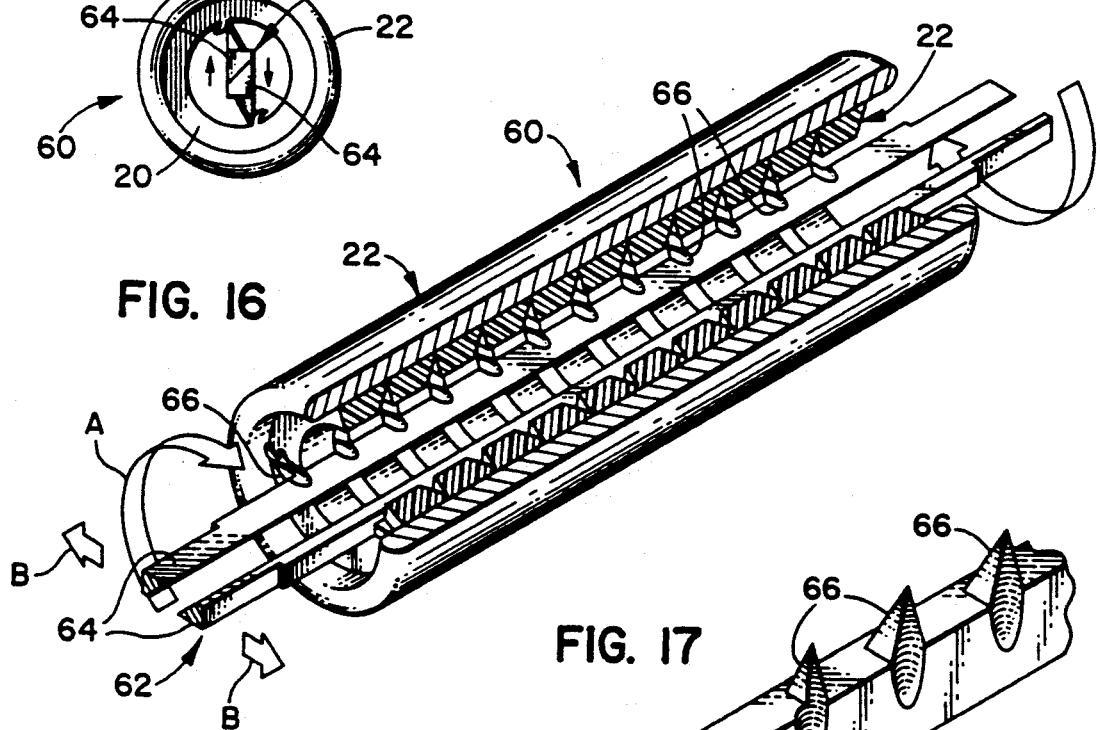
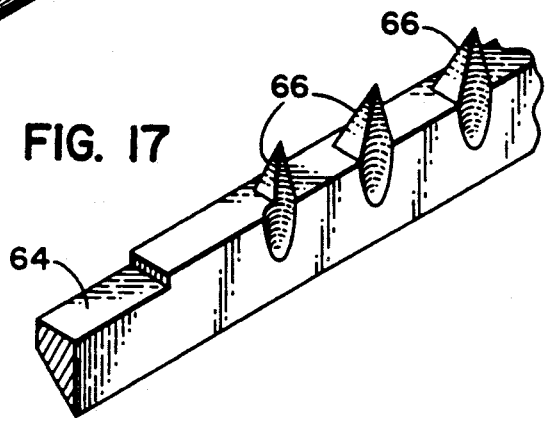
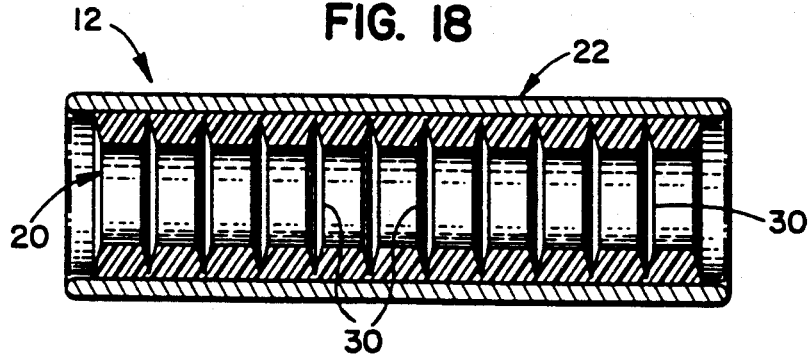

EXPANDABLE SPINAL IMPLANT AND SURGICAL METHOD

I. CROSS-REFERENCE TO RELATED APPLICATION

The present application is a continuation-i application claiming priority to commonly assigned U.S. Pat. application Ser. No. 07/439,560, filed Nov. 20, 1989, entitled "Expandable Spinal Implant and Surgical Method", now abandoned.

II. BACKGROUND OF THE INVENTION

1. Field of the Invention

This invention pertains to a surgical procedure for stabilizing the spine. The procedure includes the use of a novel implant. More particularly, this invention pertains to a novel expandable spinal implant and a novel surgical method utilizing the implant.

2. Description of the Prior Art

Chronic low back pain is one of the most common and perplexing problems facing the field of orthopedic surgery. In addition to patient discomfort, chronic low back pain has severe adverse societal impacts, including lost income and possible chronic dependence on drugs, alcohol and public relief programs.

In many cases, low back pain can be avoided by preventing relative motion between spinal vertebrae. This treatment is commonly referred to as intervertebral stabilization. To abate low back pain, stabilization is directed to stabilizing contiguous vertebrae in the lumbar region of the spine.

Surgical techniques are known for use in spinal stabilization. These techniques seek to rigidly join vertebrae which are separated by a degenerated disk. Ideally, the surgery effectively replaces the vertebra-disk-vertebra combination with a single rigid vertebra. Various surgical techniques have been developed which attempt to approach or approximate this ideal.

One technique known in the art is to partially remove a degenerated disk and insert a bone graft into the void formed by the removed disk. Other techniques involve the use of an implant which, acting along or in combination with bone fragments, replace the use of bone grafts. An example of such an implant is shown in U.S. Pat. No. 4,501,269 to Bagby dated Feb. 26, 1989. In Bagby, a large, cylindrical basket is driven into a hole formed between bones which are to be joined. The basket is hollow and is filled with bone fragments which are produced during a boring step. Bone-to-bone fusion is achieved through and about the basket. In Bagby, the hole for the basket is slightly smaller than the diameter of the basket. This structure results in the spreading of the opposing bone segments upon insertion of the basket. This results in taughtness, which provides initial stabilization. Eventual fusion of the opposing bone segments results from bone growth through the basket.

Implants such as those shown in U.S. Pat. No. 4,501,269 are promising. However, improved implant design is necessary to enhance patient safety and the probability of a satisfactory recovery.

III. SUMMARY OF THE INVENTION

According to a preferred embodiment of the present invention, and implant for insertion into a bore formed between opposing vertebrae of an animal's spine is disclosed. The implant includes an expandable body and a mechanism for expanding the body between a first state and a second state. The body includes a plurality of ribs which are deformable between first and second shapes. The exterior dimensions of the body is larger in the second shape than in the first shape. The preferred embodiment also discloses a novel surgical method involving use of the implant. In the novel method, an entrance bore is formed into the degenerated disk area of a spine. An enlarged chamber is formed between opposing vertebrae to be fused, with the enlarged chamber communicating through the exterior of the spine via the entrance bore. The vertebra implant in the first state is inserted through the entrance bore into the chamber and expanded into the second shape.

IV. BRIEF DESCRIPTION OF THE DRAWINGS

FIG. 3 is an exploded, perspective view of the implant of the present invention shown in an unexpanded shape;

FIG. 4 is a side, sectional view showing a body portion of the implant of the present invention;

FIG. 5 is a side elevation view of a tie rod for use with the present invention;

FIG. 6 is an end elevation view of a tie rod end cap for use with the present invention;

FIG. 7 is a side elevation view, partially in section, of the end cap of FIG. 6;

FIG. 14 is a top plan view of the cutting end of a tool for use in cutting radial grooves in the matrix of the assembly of FIG. 13;

FIG. 15 is an end elevation view of the assembly of FIG. 13 showing the tool tip of FIG. 14 in use;

FIG. 16 is a perspective view of the assembly of FIG. 13 showing the cutting tool end of FIG. 14 in use;

FIG. 17 is a perspective view of a portion of the cutting tool of FIG. 14;

FIG. 18 is a side sectional view of the assembly of FIG. 13 with radial grooves cut by the tool tip of FIG. 14.

V. DESCRIPTION OF THE PREFERRED EMBODIMENT

A. General

Figure 1:
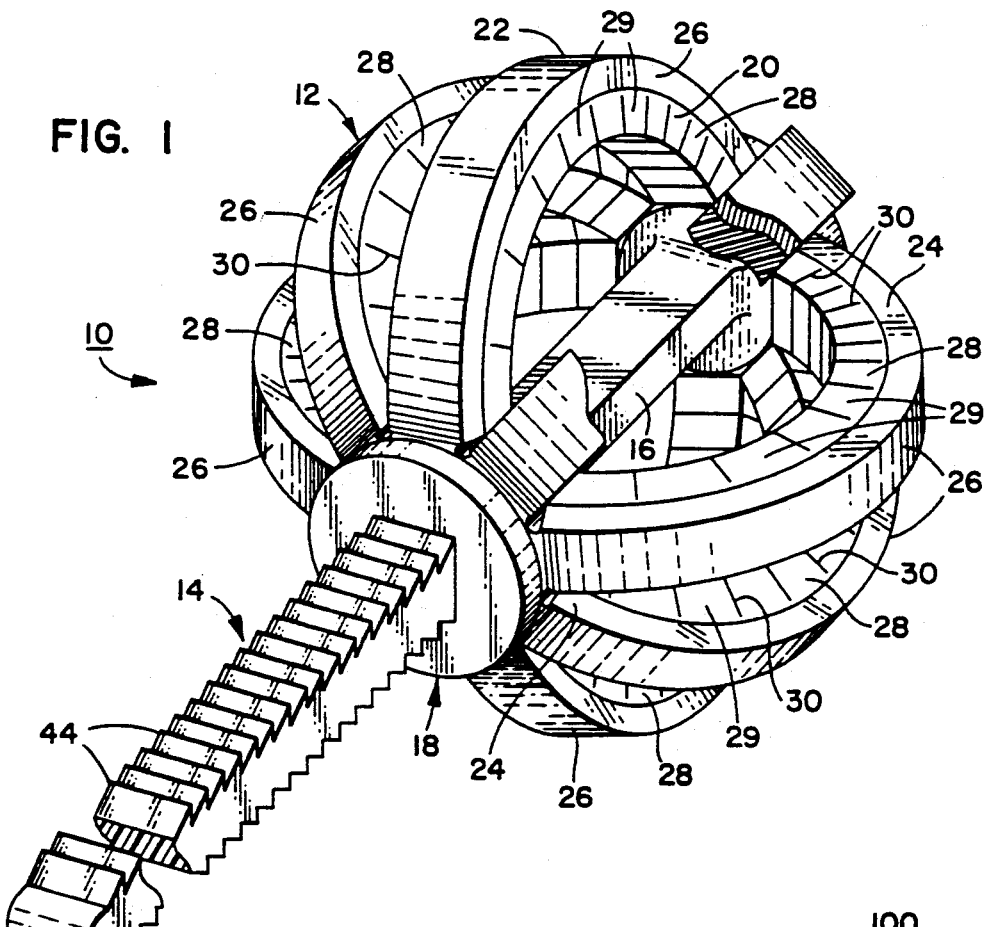
FIG. 1 is a perspective view, partially in section, showing an implant according to the present invention with the implant shown in an expanded shape.

Reference is now directed to the various figures in which identical elements are numbered identically throughout. FIG. 1 is a perspective view of an implant 10 according to a preferred embodiment of the present invention. Implant 10 includes a body 12 and an expander 14. The expander 14 includes a tie rod 16 and an attachable end cap 18.

Shown best in FIG. 3, body 12 has a rest (or first) state in which body 12 is generally cylindrical. As will be more fully described, through application of expander 14, body 12 may be deformed to an expanded (or second) state such as that shown in FIGS. 1 and 2.

B. Implant Body

The body 12 includes an inner structure 20 (conveniently referred to as a matrix) and an outer structure 22 (conveniently referred to as a shell). Shell 22 is a hollow, cylindrical tube. The tubular shell 22 has a plurality of longitudinally extending slots 24. Slots 24 are angularly displaced around the circumference of tubular shell 22 and extend through the entire thickness of tubular shell 22. However, the slots 24 do not extend the entire length of shell 22, such that the terminal ends of shell 22 (designated by number 23) are solid rings 23 through which slots 24 do not extend.

The material of outer structure 22 between slots 24 defines a plurality of outer ribs 26. As shown in FIG. 3, the ribs 26 are arranged in a generally cylindrical array, with the rings 23 holding the ribs 26 in the cylindrical array.

The inner structure or matrix 20 of body 12 includes a plurality of inner ribs 28, with each of ribs 28 disposed on an inner surface of each of outer ribs 26. A plurality of circumferential grooves 30 are cut into the inner surface of each of inner ribs 28 and spaced at intervals along the longitudinal length of ribs 28. As shown in FIG. 4, each of grooves 30 are V-shaped in cross-section, with a wide end of the grooves 30 at the inner surface of the inner ribs 28. The grooves 30 are closely spaced from, but do not extend all the way to, the outer surface of inner ribs 28. The grooves 30 divide the ribs 28 into a plurality of block segments 29.

C. Implant Expander

As previous indicated, the includes tie rod 16 and an attachable end cap 18. Shown best in FIG. 5, tie rod 16 includes an integrally molded end cap 32 having a disk-shaped force transmitting plate 34 and a frusto-conical shaped support disk 36. An annular groove 38 is formed in cap 32 between plate 34 and support disk 36.

A tie rod post 40 extends axially from disk 36 and terminates at a distal end 42. Adjacent distal end 42, post 40 is provided with a plurality of barbs 44.

As shown in FIGS. 6 and 7, attachable end cap 18 is similar to cap 32 in that cap 18 has an outer disk-shaped force transmitting plate 46 and an inner, frusto-conical support disk 48. Plate 46 and disk 48 are separated by an annular groove 50. Formed through an axis of attachable end cap 18 is a notched bore 52 with notches 54 complementarily sized to receive barbs 44 of tie rod 16.

D. Cooperative Assembly of Body 12 and Expander 14

Tie rod 16 and end cap 18 are sized to cooperate to exert a deforming force on the axially opposite ends 23 of body 12. Specifically, plates 34 and 46 of caps 32 and 18, respectively, are sized to oppose and abut ring ends 23 of body 12. Frusto-conical disks 36, 48 are sized to be received within shell 22, with disks 36, 48 opposing inner ribs 28.

Tie rod 16 is aligned to pass through bore 52, with barbs 44 captured within notches 54. By drawing on free end 42 through any suitable drawing means, tie rod 16 is urged through bore 52. The barbs 44 incrementally advance through notches 54 to draw caps 32 and 18 together while preventing separation of caps 32, 18 when the drawing force is removed from free end 42.

With plates 34, 46 sized to abut ring ends 23, the force which urges end caps 18, 32 together creates a compressive force on the axially opposite ends 23 of body 12. This force causes ribs 26, 28 to arc outwardly to the shape shown in FIGS. 1 and 2.

Figure 2:
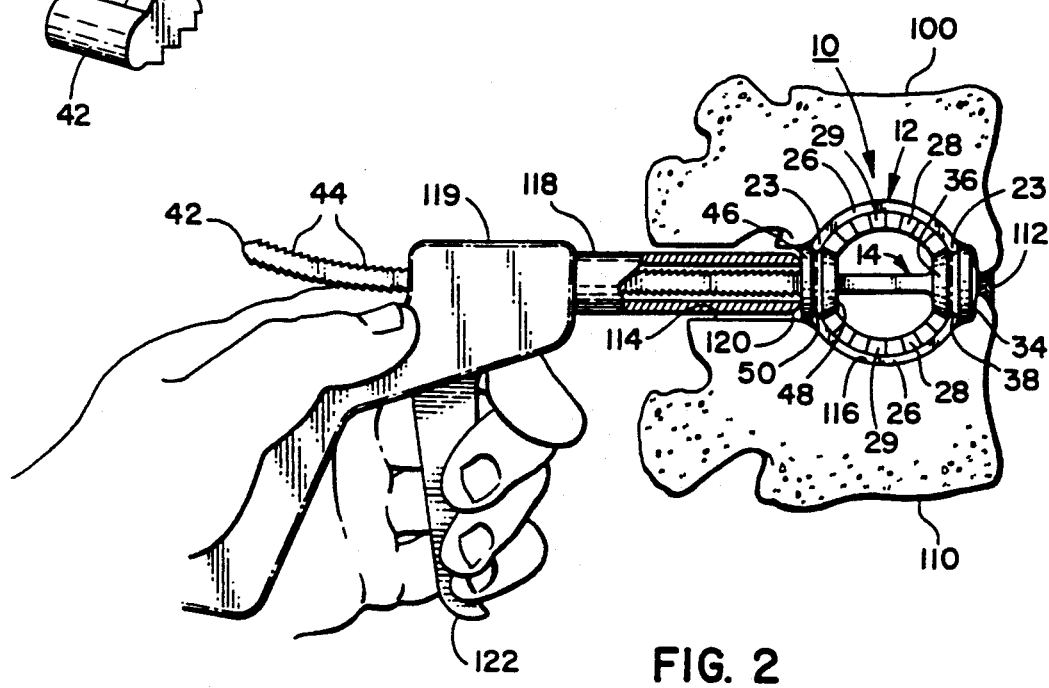
FIG. 2 is a side elevation view, partially in section, showing the implant of FIG. 1 being expanded within a chamber formed between opposing vertebrae.

As shown in FIGS. 1 and 2, the inner ribs 28 curve outwardly to a point where the opposing notch-defining surfaces of notches 30 have collapsed onto one another so that grooves 30 are closed as shown in FIGS. 1 and 2. Best shown in FIG. 2, frusto-conical disks 36, 48 are shaped to oppose and abut the ends of inner ribs 28 when ribs are fully arched. Grooves 38, 50 are sized to receive rings 23 as the shell 22 deforms to the expanded shape of FIG. 2.

Figure 2A:
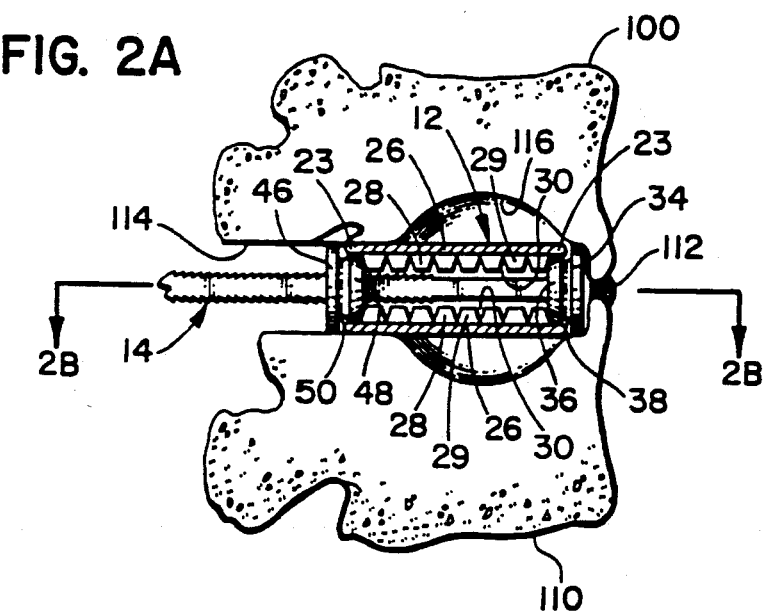
FIG. 2A is a view of FIG. 2 showing the implant in an unexpanded state.
Figure 2B:
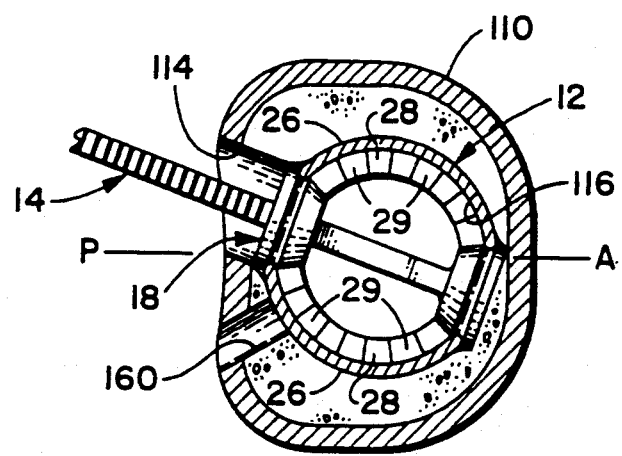
FIG. 2B is a top plan view of a vertebra body showing an expanded implant within the chamber formed between the opposing vertebra.
Figure 8:
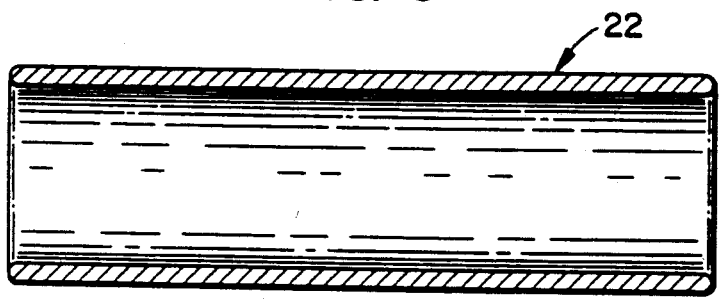
FIG. 8 is a side sectional view of an outer shell for use in the construction of the implant of the present invention.
Figure 9:
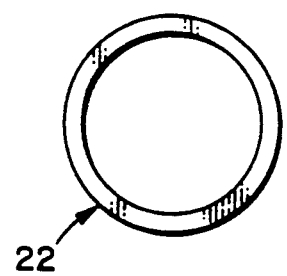
FIG. 9 is an end elevation view of the shell of FIG. 8.

As shown best in a comparison between FIGS. 2A and 2B, the ribs 28 are shown expanded between the first shape (FIG. 2A) and the second shape (FIG. 2B). In the first shape, the ribs 28 are generally straight with the opposing surfaces of contiguous block segments 29 being spaced apart. In the expanded shape of FIG. 2B, the opposing surfaces of the block segments 29 are touching. As a result, the arch shaped rib 28 is now load bearing. The structural integrity of the arched rib 28 (as shown in FIG. 2B) is similar to the load bearing characteristics of stone arches in architecture. The shape of the block segments 29 is voussoir-shaped. ("Voussoir" being recognized as the wedged shaped stones which comprise architectural arches.) With each of the blocks at least partially touching, the load bearing integrity of the arched rib 28 is maintained.

E. Preferred Materials of Construction

The preferred embodiment, described above, illustrates body 12 as being a composite of an inner structure (or matrix) 20 and an outer structure (or shell) 22. This composite structure is selected so that materials of different properties can be used for forming inner ribs 28 and outer ribs 26.

Preferably, outer ribs 26 are formed of a material which is highly resistant to tensile forces. On the other hand, inner ribs 28 are formed from a material which is highly resistant to compressive forces. The high resistance to compressive forces of inner ribs 28 requires the formation of grooves 30, which are closed as inner ribs 28 are bent to the fully arched position shown in FIGS. 1 and 2.

As will be described, it is anticipated that the implant 10 will be preferably used in surgery in spines of humans as well as other animals. Accordingly, the material of inner structure 20, outer structure 22, and expander 14 should be biocompatible. Often, it is preferable that the material of these elements be radiolucent so that they will not interfere with X-ray examination of a patient's recovery. A preferred material for expander 14 (including tie rod 16, cap 18 and cap 32) is polyethylene. This material is biocompatible, radiolucent, and has sufficient flexibility for barbs 44 to be advanced through notched bore 52 in one direction in response to a drawing force on end 42, but maintain a fixed position in the absence of the force 42.

A preferred material for the outer structure 22 is carbon fiber. This material should permit the outer structure 22 to bend, but not stretch. Accordingly, the outer structure 22 and outer ribs 26 hold the inner ribs 28 in place and prevent breakage of ribs 28. Carbon fiber is known to be biocompatible and radiolucent.

The material of the inner ribs 28 is preferably polymethyl methacrylate. This material is rigid and resistant to compression. From widespread use as a bone cement and joint replacement, this material is known to be biocompatible and radiolucent. With the combination of materials, the expanded implant 10 is a rigid ball-like structure which is resistant to compression.

As a result of the structure of the present invention, the expander ribs 28 are straight in a rest position but assume an arch shape when expanded. The arch is a combination of individual building blocks of compression resistant material. The building blocks are the material between grooves 30. An arch formed of blocks of compression resistant material is highly resistant to forces acting to collapse the arch.

It will be appreciated that the foregoing recitation of materials is to illustrate a presently preferred construction. It is not an intent to limit the present application to the disclosed materials. For example, it may be desirable to form elements of the implant from resorbable material. For example, the outer ribs 26 could be formed of tightly woven suture material such as polyglycolic acid. Inner ribs 28 could be formed of any biocompatible ceramic such as hydroxyapatite or tricalcium phosphate.

F. Method of Construction

Figure 10:
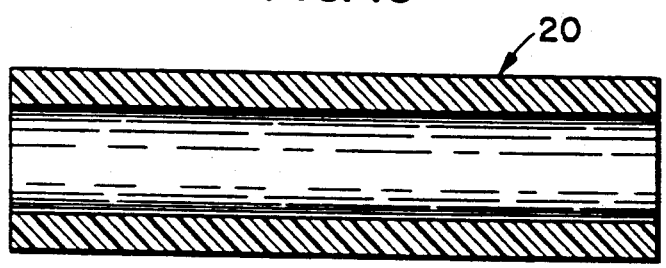
FIG. 10 is a side sectional view of a matrix for use in the construction of the present invention.
Figure 11:
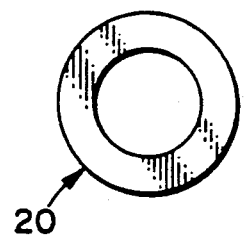
FIG. 11 is an end elevation view of the matrix of FIG. 10.

With best reference to FIGS. 4 and 8-18 of the drawings, the method of construction of body 12 will now be described. As shown in FIGS. 4 and 8-10, the starting materials of the construction include a cylindrical outer structure 22 (FIGS. 8 and 9) and a cylindrical inner structure 20 (FIGS. 10 and 11).

As previously indicated, tubular outer structure 22 is a tube of carbon fiber. Tubular inner structure 20 is a tube of polymethyl methacralate. Inner structure 20 is sized to be axially received within outer structure 22, with a close tolerance between structures 20 and 22. The axial length of inner structure 20 is sized to be slightly less than the axial length of the outer structure 22.

Figure 12:
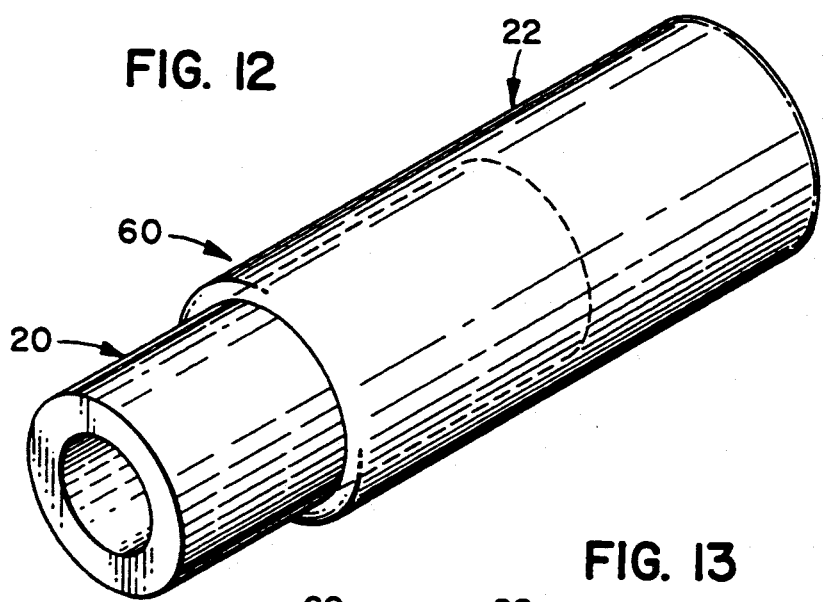
FIG. 12 is a perspective view showing the matrix of FIG. 10 being partially inserted within the shell of FIGS. 8 and 9.
Figure 13:
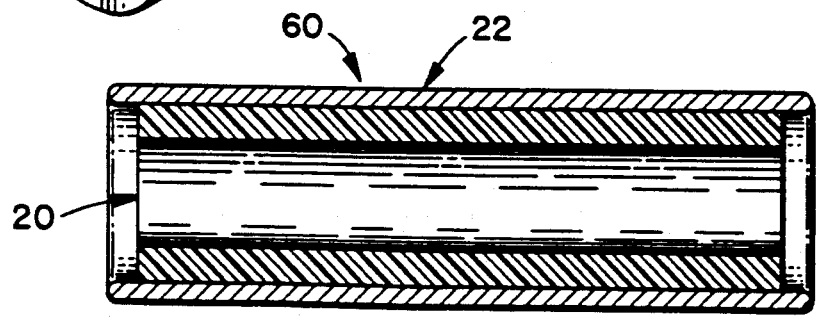
FIG. 13 is a side sectional view showing an assembly comprising the matrix of FIG. 10 fully inserted within the shell of FIGS. 8 and 9.

Structures 20 and 22 are joined into a completed assembly 60, as shown in FIG. 13. Assembly 60 is formed by sliding inner structure 20 into outer structure 22 as shown in FIG. 12. Inner structure 20 is adhered to the inner surface of outer structure 22 through any suitable mean, such as adhesives or the like.

With assembly 60 formed as shown in FIG. 13, circumferential grooves 30 may now be cut into the inner matrix 20. A preferred tool 62 for cutting grooves 30 is shown in FIGS. 14-17.

Tool 62 includes a pair of blade support rods 64 (only one of which is shown in FIG. 17). Each of rods 64 carries a row of V-shaped cutting teeth 66. The shape of teeth 66 is selected so that the teeth 66 will cut V-shaped grooves 30.

Rods 64 and teeth 66 are selected so that rods 64 may be placed together (as shown in FIG. 15) with the points of teeth 66 just beginning to cut into matrix 20 when the rods 64 are axially positioned within matrix 20 and rotated about the axis.

As shown best in FIG. 16, grooves 30 are cut by simultaneous rotation of tool 62 about the axis of assembly 60 (i.e., rotation in the direction of arrow A) and separation of rods 64 in the direction of arrows B. Accordingly, as the tool 62 is rotated and separated, the teeth 66 cut grooves 30 of progressively increasing depths until the teeth 66 are cutting close to, but not through, the outer surface of matrix 20. FIG. 18 shows the partially-completed body 12 where grooves 30 are formed in matrix 20, but without axial slots 24 having been cut through the assembly 60.

With the assembly 60 as formed in FIG. 18, the body 12 may be completed by cutting axial slots 24 through both the inner matrix 20 and the outer shell 22. The slots 24 may be cut through any suitable means, and are best shown in FIG. 4 as having been cut completely through the thickness of inner matrix 20 and outer shell 22. The length of slots 24 are selected so that they cut through the entire axial length of matrix 20 but do not cut through the entire length of outer shell 22. With the method of construction thus described, the entire body 12 is completed.

G. Novel Surgical Method

1. Formation of Entrance Bore

As indicated, the implant 10 is preferably used in spinal stabilization surgery. FIG. 2 of the drawings shows vertebrae 100 and 110 separated by disk material 112.

After identifying a diseased disk 112, the surgeon forms a bore 114 through the disk layer 112. The bore 114 is formed through any conventional means by using a surgical drill bit (not shown). The bit is sized such that the diameter of the bore 114 is approximately sized to be the external diameter of the implant body 12 when in the relaxed or first state as shown in FIG. 3. The depth of the bore 114 is controlled so that the axial length of the body 12 may be fully inserted within the bore, with the body 12 fully located between opposing vertebrae 100, 110.

While the diameter of body 12 and bore 114 will vary from patient to patient, there is a practical maximum size of the diameter of bore 114 for any given patient. This maximum is attributed to the fact that too large of a drill bit cannot be passed through the patient's body and placed against disk tissue 112. If too large a drill bit is used, the size of the bit will interfere and possibly damage other anatomical parts, such as important blood vessels, nerves, etc.

A typical selected diameter of body 12 (when in the first state) and bore 114 is preferably about 12 mm. This diameter is selected for bore 114 to cut through disk material separating the fourth and firth lumbar vertebrae in a human spine in a typical adult human male. The depth of the intervertebral space between the fourth and fifth lumbar vertebrae in an adult human male (measured as the anterior-posterior dimension of the vertebrae) is commonly about 35 mm. As a result, a preferred length of body 12 will be about 25 mm so that the body 12 may be fully received within and between opposing vertebrae.

It will be appreciated that the foregoing dimensions and descriptions have been given with respect to a particular vertebrae location in the spine of an adult human male. It is anticipated the present implant and method could be used on any animal spine. Accordingly, the dimensions of the implant 10 and entrance bore 114 will vary proportionately with increases or decreases in spinal anatomy between different animal types. Also, in humans, the dimension will vary with numerous factors, including anatomic region of the spine, age and sex. For example, the implant and surgical method is not limited to the lumbar region, and may be utilized in other regions of the spine where vertebrae dimensions may be different than those described. Therefore, several different sizes of the implant 10 are anticipated so a surgeon can select the optimum implant 10 for a given patient.

2. Formation of Enlarged Chamber

With the entrance bore 114 formed as described, the surgeon then cuts a hollow spherical chamber 116 between the opposing vertebrae 100 and 110. The chamber 116 is sized to be complementary to the exterior dimensions of the implant 12 in the enlarged state.

Since the chamber 116 has greater volume than a bore 114, the cutting of chamber 116 removes greater amounts of disk material and exposes a greater surface area of the opposing vertebrae bone material. The exposure of the additional surface area increases the probability of successful grafting between the opposing vertebrae 100, 110.

The formation of the enlarged spherical chamber 116 can be formed through any suitable technique. Preferably, the chamber 116 is formed through the use of an intervertebral reamer such as that shown and described in U.S. Pat. No. 5,015,255 and copending U.S. Pat. application Ser. No. 07/350,050, filed on May 10, 1989, which names myself and James D. Corin as joint inventors.

The diameter of the chamber 116 (and hence, the maximum allowable diameter of the expanded implant 10) is selected to provide a clearance so that the chamber 116 is not cut through the sides of the vertebrae. This diameter will vary from patient to patient, and between locations in the spine. However, to provide a clearance of about 11 mm of the sides of the vertebrae, the chamber is preferably held to a maximum diameter of about 22 mm.

3. Insertion and Expansion of Implant

With the enlarged chamber 116 so formed, the surgeon places implant 10 in the unexpanded state into bore 114, the molded end cap 32 is adjacent the anterior side of the spine. The free end 42 of the rod 16 is exposed to the surgeon.

In FIG. 2A, an unexpanded implant 10 is shown inserted within an enlarged chamber 116. In the position shown in FIG. 2A, the implant 10 is not urging vertebra 100, 110 apart. Accordingly, the annulus (the fibrous outer circumferential portion of disk 112) connecting the vertebra 100, 110 is shown in a relaxed or unstretched state.

With the implant 10 so inserted, the surgeon then draws on tie rod 16 to force implant 10 to expand to the second shape as shown in FIG. 2. The mechanism by which the surgeon applies the compressive force to the implant 10 may be any suitable method. In FIG. 2, the surgeon is shown using a ratchet gun 119 for applying the compressive force. Ratchet guns are well known and form no part of this invention per se.

The gun 119 has a barrel end 118 which is sized to be received within bore 114. A free end 120 of barrel end 118 abuts plate 46 of attachable cap 18. The barbed rod 40 passes through barrel 118. The barbs 44 are advanced through a ratchet mechanism (not shown) actuated by the surgeon's operation of a ratchet gun trigger 122.

The surgeon continues to draw the barbed end of the tie rod 16 through the ratchet gun 119 until the implant 10 is expanded to the fully expanded state. As it expands, the outer surfaces of the implant 10 abut against the opposing surfaces of the vertebrae 100, 110. Continued expansion of the implant 10 causes the vertebrae 100, 110 to stretch apart slightly. This stretching acts to tighten the annulus of disk 112, which has not been removed through the formation of bore 114 and chamber 116. Those skilled in the art will recognize the annulus as being the fibrous outer circumferential portion of the disk 112. The stretching and tightening of the annulus provides initial stabilization between the opposing vertebrae. So that stretching will occur, the external dimensions of chamber 116 are preferably sized to be about 3 mm less than the external dimensions of the implant 10 measured in the fully expanded state.

With the implant 10 fully expanded, the surgeon removes the ratchet gun and severs the excess barbed end of the tie rod 16.

4. Use of a Graft Medium

While the patient may now be closed, it is preferable that the chamber 116 be filled with a graft medium to facilitate fusion between the opposing vertebrae 100, 110. The preferred graft medium would be finely chopped cortical or cancellous bone chips.

FIG. 2B shows a preferred method for admitting the graft medium into chamber 116. As shown in FIG. 2B, the entrance bore 114 is drilled to the side of the anterior-posterior axis (A-P) of the patient. An access bore 160 is formed through the vertebra 100 on the opposite side of the axis (A-P). The surgeon can then impact bone chips into chamber 116 through bore 160. The bone chips are admitted into the chamber 116 by passing them through opposing ribs 26 of the expanded implant body 12.

An alternative method of admitting bone chips into chamber 116 is to fill the chamber 116 with a bone chip slurry before inserting the implant 10 into the chamber 116. Also, the implant 10 could also be impregnated with a bone chip slurry before being passed into the chamber 116.

With the graft medium in place, the surgeon can then close the patient through any suitable technique.

The grafting of bone chips results in a fusion between the vertebrae bodies 100, 110. While the fusion process is taking place, the surgeon can readily monitor the patient's progress since the preferred materials of the implant 10 are radiolucent and will not interfere with X-ray examination. Also, during the fusion process, the implant 10 is self-retaining in a rigid, generally spherical shape. The rigidity of the enlarged implant 10, together with the stretching of the annulus, provides stabilization between vertebrae 100, 110 during the fusion process.

H. Alternative Embodiments

1. Expanded Implant with Netting

Referring now to FIGS. 19–22, an alternative embodiment of the present invention is shown. In the alternative embodiment a netting 200 is provided surrounding the implant body 12. Except for the addition of the netting 200, the implant is identical to that shown in FIG. 1 and similar elements will be numbered identically.

Figure 19:
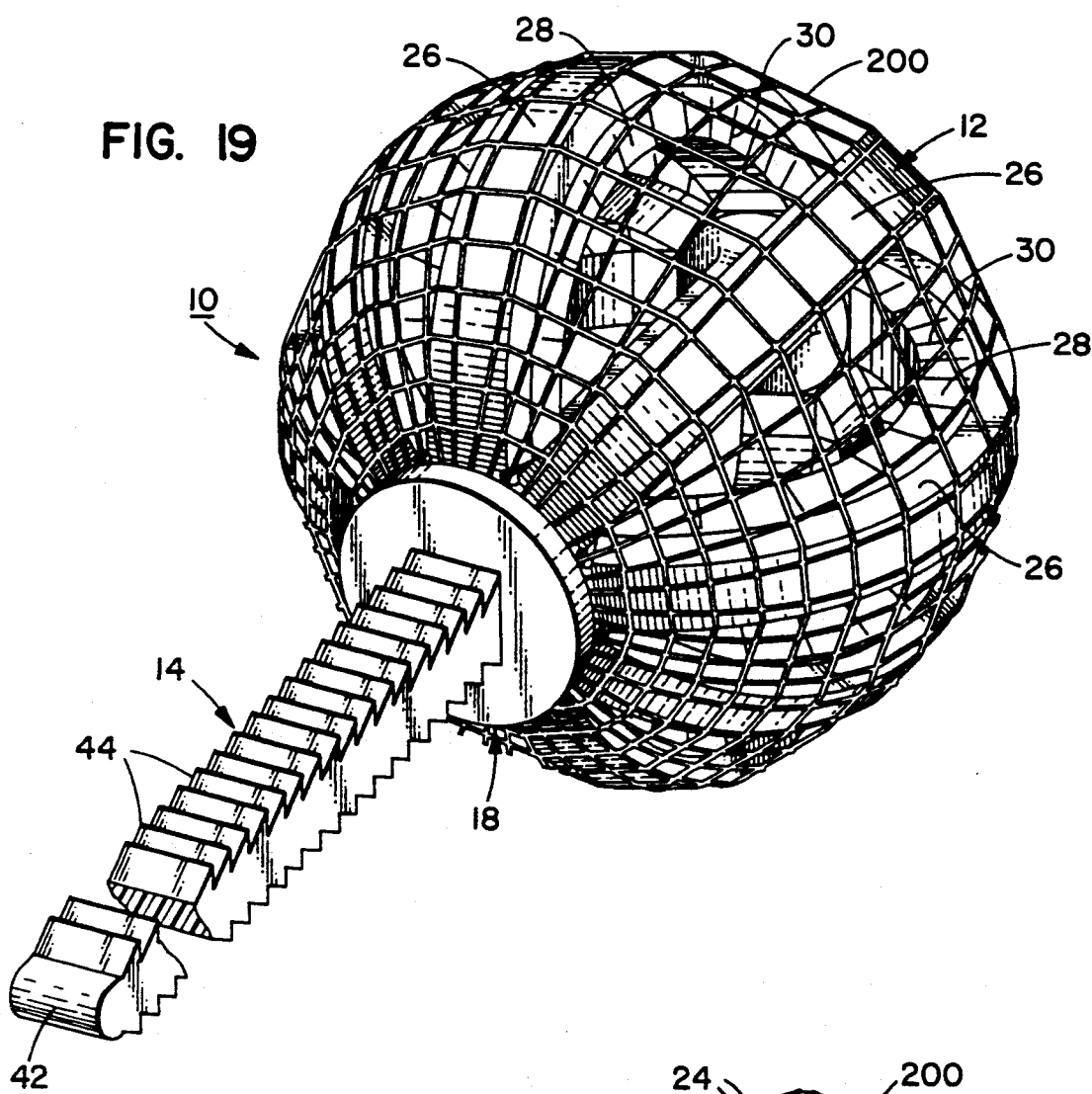
FIG. 19 is a perspective view showing an implant according to an alternative embodiment of the present invention with the implant shown in an expanded shape.
Figure 21:
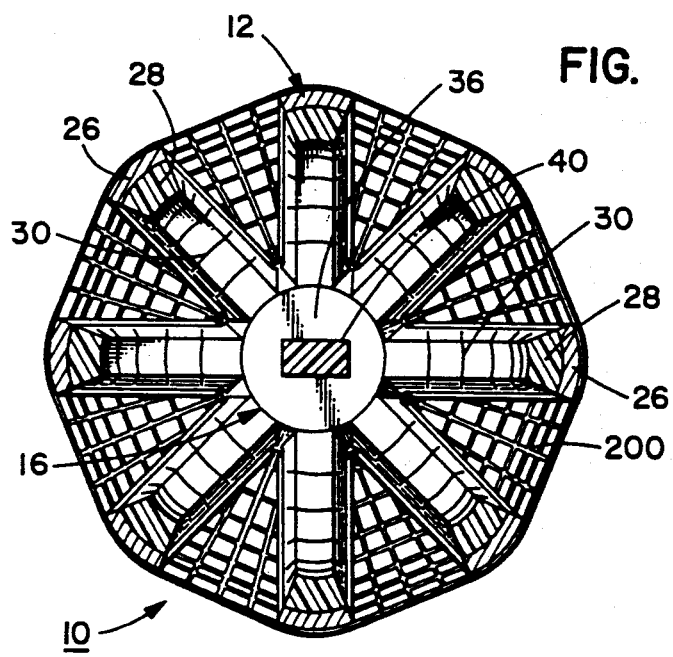
FIG. 21 is a cross-sectional view of the expanded implant of FIG. 19.

In use of the embodiment of FIG. 1, there is a concern that the ribs 26 could sink into soft bone material of the patient's vertebra. To prevent this, a fiber netting 200 (preferably of nylon or polyethylene) surrounds the body portion 12. In a preferred embodiment, the netting 200 presents openings of about 1 millimeter in size. The netting is bonded through any suitable means (such as adhesive or heat bonding) to the outer surface of the ribs 26. The size of the netting 200 is selected such that when the implant 10 is expanded to its fully expanded position (as shown in FIGS. 19 and 21) the netting is taut resulting in a hard ball shape which prevents sinking into the bone tissue.

Figure 20:
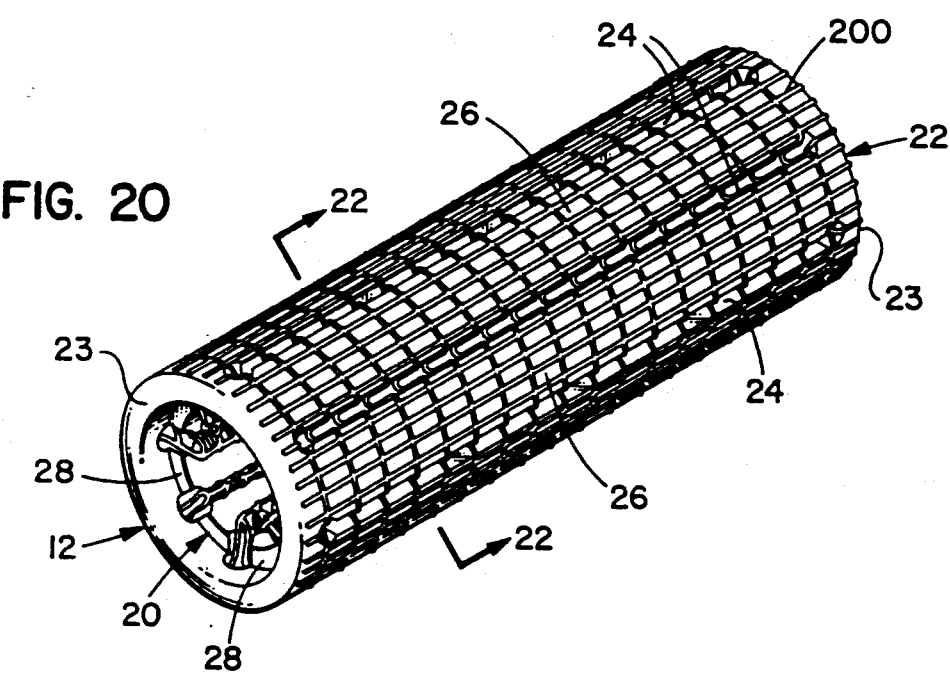
FIG. 20 is a perspective view of a body portion of the implant of the alternative embodiment of FIG. 19.
Figure 22:
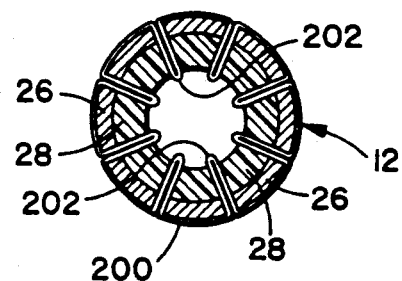
FIG. 22 is a cross-sectional view of the body portion of FIG. 20.
Figure 24:
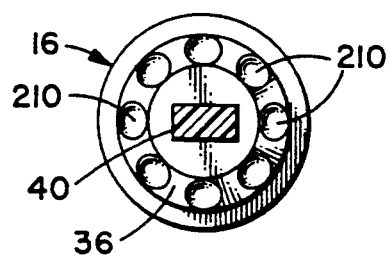
FIG. 24 is a front plan view of a tie rod end cap of the embodiment of FIG. 23.

As shown in FIGS. 20 and 22, in the unexpanded shape, the netting between the ribs 26 is forced downwardly into the implant body 12 through opposing ribs 26 to define a plurality of inwardly projecting pleats 202. As a result, in the unexpanded shape, the netting does not interfere with the exterior dimensions of the implant body 12. Accordingly, the implant body 12 may be readily inserted into the bore 114 formed between opposing vertebra (as shown in FIGS. 1 and 2A).

The reader will recall that the outer ribs 26 retain the inner ribs 28 while the inner ribs are being deformed to the arch shape. A further alternative embodiment (not shown) could be the elimination of the outer rib material 26 with the netting 200 bonded directly to the inner ribs 28 to hold them in place as they are being expanded to the arch shape.

Above, the preferred material of the netting 200 was identified as nylon or polyethylene. An alternative material would be any resorbable material such as loose woven suture material (e.g. polyglycolic acid).

2. Ball and Socket Connection

As shown in FIGS. 4, 5 and 7, the inner rib 28 includes a plurality of cuts 30 which separate the rib 28 into a plurality of blocks 29 having flat opposing surfaces. The flat opposing surfaces will abut flat surfaces such as surface 48 of end cap 18 (see FIG. 7).

Figure 23:
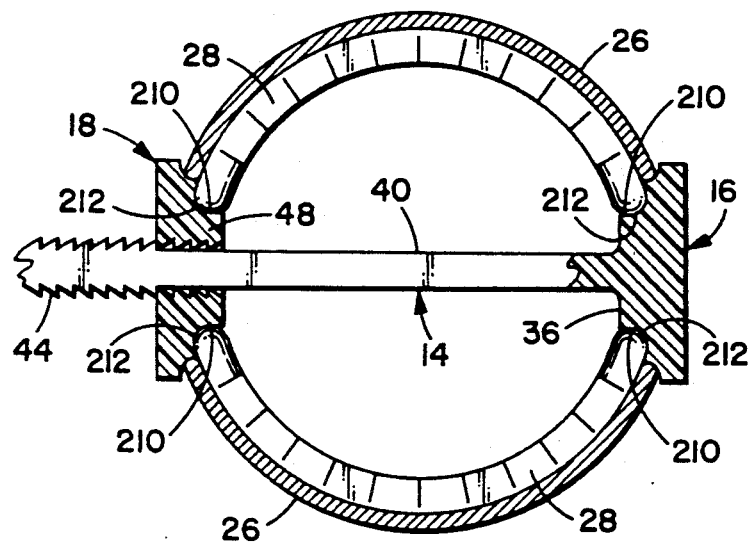
FIG. 23 is a side elevation view, shown in section, of an expanded implant according to a second alternative embodiment of the present invention.

To ensure maximum load transmission between the ribs 28 and the end caps 32, 18, a second alternative embodiment provides for hemispherical concave indents 210 formed on the frusto-conical disks 36, 48. Correspondingly, the end portions of the ribs 28 are provided with convex hemispherical surfaces 212. Surfaces 212 are sized to be complimentarily received within detents 210. As a result, as the ribs 28 are expanding to the arched position (shown in FIG. 23), surfaces 212 are freely sliding within detents 210. This ensures maximum surface area contact between the ribs 28 and the surfaces 36, 48.

An alternative to the spherical ball and socket geometry would be a cylindrical geometry (not shown). Namely, convex cylindrical rounded ends of ribs 28 could be received in concave and complementary cylindrical rounded detents in disks 36, 48. With cylindrical axis being transverse to the longitudinal dimension of the implant, the cylindrical geometry will prevent lateral motion while accommodating the arching of the ribs 28.

From the foregoing, it can be seen how the present invention has been attained in a preferred manner. Modifications and equivalents of the disclosed concepts while readily occur to those skilled in the art are intended to be included within the scope of the invention. Thus, the scope of the invention is intended to be limited only by the scope of the claims which, are, or may hereafter be, appended hereto.

I claim:

1. A spinal implant for insertion into a bore formed between opposing vertebrae of a spine, said implant comprising:
    a plurality of deformable ribs;
    said ribs deformable in response to a deforming force to change from a first shape to a second shape;
    said ribs in said first shape presenting exterior surfaces cooperating to define a first exterior dimension sized to be received within a bore formed between adjacent vertebrae of a spine;
    said ribs in said second shape presenting exterior surfaces cooperating to define a second exterior dimension greater than said first exterior dimension and sized to urge said adjacent vertebrae apart;
    applying means for applying said deforming force to said ribs.

2. An implant according to claim 1 further comprising retaining means for retaining said ribs in said second shape.

3. An implant according to claim 1 wherein opposing interior surfaces of opposing ones of said ribs in said second shape cooperate to define a chamber, with passage means for defining a passageway between said chamber and an exterior of said implant.

4. An implant according to claim 3 wherein said passage means is defined by opposing side surfaces of adjacent ones of said ribs defining openings extending through said implant and into said chamber.

5. An implant according to claim 1 wherein said implant is formed of a biocompatible material.

6. An implant according to claim 1 wherein said ribs in said first shape extend generally longitudinally;
    said applying means including means for applying said deforming force to urge opposite ends of said ribs toward one another with said ribs having central areas deforming outwardly.

7. An implant according to claim 1 wherein
    said first exterior dimension is sized for said implant to be passed through an entrance dimension of said bore and said second exterior dimension is sized greater than said entrance dimension.

8. An implant according to claim 7 wherein said second exterior dimension is sized for opposite ones of said ribs to be urged against opposing surfaces of said opposing vertebrae when said ribs are deformed to said second shape.

9. An implant according to claim 1 wherein said implant is sized to be received with a bore formed between adjacent vertebrae of a human spine.

10. A spinal implant for insertion into a bore formed between adjacent vertebrae of a spine, the implant comprising:

a plurality of ribs, each of said ribs including an inner structure and an outer structure, said inner structure having a plurality of grooves formed in an inner surface of said inner structure and spaced along a length of said ribs for such inner structure to curve outwardly from a rest state to an expanded state in response to a deforming force applied to opposite ends of said rib, said outer structure including means surrounding an outer surface of said inner structure to retain said inner structure in an arcuate shape when deformed by said deforming force;

said implant sized to be inserted within a bore formed between adjacent vertebrae of a spine when said ribs are in said rest state, said implant sized to urge said adjacent vertebrae apart when said ribs are in said expanded state;

means for applying said deforming force to said opposite ends.

11. A spinal implant for insertion into a bore formed between opposing vertebrae of a spine, the implant comprising:

a plurality of ribs, each of said ribs including an inner structure and an outer structure, said inner structure having a plurality of grooves formed in an inner surface of said inner structure and space along a length of said ribs for such inner structure to curve outwardly in response to a deforming force applied to opposite ends of said rib, said outer structure including means surrounding an outer surface of said inner structure to retain said inner structure in an arcuate shape when deformed by said deforming force;

means for applying said deforming force to said opposite ends;

said inner structure is formed of a compression resistant material and said outer structure is formed of a tension resistant material, said inner and outer structures disposed in overlying relation.

12. A spinal implant for insertion into a bore formed between opposing vertebrae of a spine, the implant comprising:

a plurality of ribs, each of said ribs including an inner structure and an outer structure, said inner structure having a plurality of grooves formed in an inner surface of said inner structure and spaced along a length of said ribs for such inner structure to curve outwardly in response to a deforming force applied to opposite ends of said rib, each of said grooves extending between groove defining surfaces of said inner surface, said outer structure including means surrounding an outer surface of said inner structure to retain said inner structure in an arcuate shape when deformed by said deforming force;

means for applying said deforming force to said opposite ends;

said inner and outer structures extend in generally a longitudinal direction, said groove defining surfaces of said inner structure movable toward one another into abutting relation as said ribs are deformed from said first shape to said second shape.

13. An implant according to claim 10 wherein said implant is sized to be received within a bore formed between opposing vertebrae of a human spine.

14. A method for manufacturing an implant for insertion into a bore formed between opposing vertebrae of a spine, said method including the steps of:

providing an implant shell having a hollow interior and an implant matrix having a hollow interior, wit said matrix sized to be received within said shell in close fitting relation;

inserting said matrix into said shell to form a composite implant assembly;

forming a plurality of circumferential cuts along an inner surface of said matrix and with said cuts spaced along a longitudinal length of said matrix;

forming a plurality of longitudinal slots through both said shell and said matrix;

15. In the stabilization of a spine using an implant having a plurality of deformable ribs which are deformable in response to a deforming force to change from a first shape to a second shape, said ribs in the first shape presenting exterior surfaces defining a first exterior dimension and said ribs in said second shape presenting exterior surfaces cooperating to define a second exterior dimension greater than said first dimension, said implant further having a force applying means for applying said deforming force to said ribs, a method comprising the steps of:

locating a degenerated disk between two opposing vertebrae;

forming a bore at least partially through said disk;

inserting a leading end of said implant into said bore;

applying said deforming force to said ribs to urge said ribs to said second shape with said ribs in said second shape urging against said opposing surfaces; and fixing said ribs in said second shape.

16. A method according to claim 15 wherein said ribs in said second shape present opposing surfaces defining a chamber in communication with an exterior of said implant, said method further including the step of filling said chamber with a graft medium.

17. A method according to claim 15 ,further comprising forming said bore to have interior dimensions greater than an entrance opening of said bore, with said interior dimensions sized to receive said ribs in said second shape and with said entrance opening sized to pass said implant when said ribs are in said first shape.

18. A method according to claim 17 wherein said ribs in said second shape present a generally spherical implant and said ribs in said first shape present a generally cylindrical implant;

said method including the step of forming said entrance opening to have a diameter sized to pass said generally cylindrical implant, said interior dimension of said bore selected to define a generally spherical chamber sized to complementarily receive said generally spherical implant.

19. A method according to claim 17 wherein said interior dimensions are sized slightly less than said second exterior dimension, said method including the step of deforming said ribs to said second state and separating said vertebrae by said expanding ribs urging against said vertebrae.

20. A method according to claim 19 wherein said implant is sized to be received within a bore formed between opposing vertebra of a human spine.

21. A spinal implant for insertion into a bore formed between opposing vertebrae of a spine, said implant comprising:
- a plurality of deformable ribs;
- said ribs deformable in response to a deforming force to change from a first shape to a second shape;
- said ribs in said first shape presenting exterior surfaces cooperating to define a first exterior dimension;
- said ribs in said second shape presenting exterior surfaces cooperating to define a second exterior dimension greater than said first exterior dimension;
- applying means for applying said deforming force to said ribs;
- said ribs formed of a plurality of block segments, block segments of a rib cooperating for said rib to form an arch of abutting segments when said ribs are in said second shape.

22. A spinal implant for insertion into a bore formed between opposing vertebrae of an animal spine, the implant comprising:
- a plurality of ribs, each of said ribs including an inner structure and an outer structure, said inner structure having a plurality of grooves formed in an inner surface of said inner structure and spaced along a length of said ribs for such inner structure to curve outwardly in response to a deforming force applied to opposite ends of said rib, said outer structure including means surrounding an outer surface of said inner structure to retain said inner structure in an arcuate shape when deformed by said deforming force;
- means for applying said deforming force to said opposite ends;
- said ribs formed of a plurality of block segments, block segments of a rib cooperating for said rib to form an arch of abutting block segments when said ribs are in said second shape.

23. A method according to claim 15 wherein said ribs are formed of a plurality of block segments, said block segments cooperating to form an arch of abutting block segments when said ribs are in said second shape.

24. A spinal implant for insertion into a bore formed between opposing vertebrae of a spine, said implant comprising:
- a plurality of deformable ribs;
- said ribs deformable in response to a deforming force to change from a first shape to a second shape;
- said ribs in said first shape presenting exterior surfaces cooperating to define a first exterior dimension;
- said ribs in said second shape presenting exterior surfaces cooperating to define a second exterior dimension greater than said first exterior dimension;
- applying means for applying said deforming force to said ribs; and
- a netting surrounding said ribs.

25. A spinal implant for insertion into a bore formed between opposing vertabrae of a spine, the implant comprising:
- a plurality of ribs, each of said ribs including an inner structure and an outer structure, said inner structure having a plurality of grooves formed in an inner surface of said inner structure to curve outwardly in response to a deforming force applied to opposite ends of said rib, said outer structure including means surrounding an outer surface of said inner structure to retain said inner structure in an arcuate shape when deformed by said deforming force;
- means for applying said deforming force to said opposite ends;
- a netting surrounding said ribs.

26. An implant according to claim 10 comprising a netting surrounding said ribs.

27. An implant according to claim 26 wherein said netting is sized to be taut upon deformation of said ribs to said second shape.

28. An implant for insertion into a bore formed between opposing vertebrae, said implant comprising:
- a plurality of ribs each including a plurality of voussoir-shaped blocks with said ribs deformable in response to a deforming force to change from a first shape to a second shape, said ribs in said first shape being generally linear with opposing surfaces of contiguous blocks being spaced apart and said ribs in said second shape being arched with opposing surfaces of said contiguous blocks being in at least partial contact; and
- applying means for applying said deforming force to said ribs.

29. An implant according to claim 1 wherein said implant is formed, at least in part, from a resorbable material.

* * * * *

UNITED STATES PATENT AND TRADEMARK OFFICE
CERTIFICATE OF CORRECTION

PATENT NO. : 5,059,193
DATED : October 22, 1991
INVENTOR(S) : Stephen D. Kuslich It is certified that error appears in the above-identified patent and that said Letters Patent is hereby corrected as shown below:

Column 1, line 7, "i application" should read --in-part application--;

Column 3, line 63, insert --expander mechanism 14-- after the word "the";

Column 11, claim 11, line 32, "space" should read --spaced--;

Column 12, claim 14 line 8, "wit" should read --with--;

Column 12, claim 19 line 62, "dimension" should read --dimensions--;

Column 14, claim 25 line 19, insert --and spaced along a length of said ribs for such inner structure-- after the word "structure".

Signed and Sealed this

Eighth Day of June, 1993

Attest:

MICHAEL K. KIRK

*Attesting Officer*   *Acting Commissioner of Patents and Trademarks*